United States Patent
Salciccioli et al.

(10) Patent No.: US 9,896,393 B2
(45) Date of Patent: Feb. 20, 2018

(54) PROCESS FOR PREPARING DIALKYLBIPHENYL ISOMER MIXTURES

(71) Applicant: ExxonMobil Chemical Patents Inc., Baytown, TX (US)

(72) Inventors: Michael Salciccioli, Houston, TX (US); Tan-Jen Chen, Kingwood, TX (US); Neeraj Sangar, League City, TX (US); Ali A. Kheir, Sugar Land, TX (US); Aaron B. Pavlish, Humble, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 340 days.

(21) Appl. No.: 14/723,546

(22) Filed: May 28, 2015

(65) Prior Publication Data
US 2015/0361011 A1  Dec. 17, 2015

Related U.S. Application Data

(60) Provisional application No. 62/012,024, filed on Jun. 13, 2014.

(51) Int. Cl.
  C07C 6/06  (2006.01)
  C07C 2/74  (2006.01)
  C07C 5/367  (2006.01)
  C07C 5/10  (2006.01)
  C07C 6/12  (2006.01)

(52) U.S. Cl.
  CPC .................. *C07C 2/74* (2013.01); *C07C 5/10* (2013.01); *C07C 5/367* (2013.01); *C07C 6/126* (2013.01); *C07C 2523/42* (2013.01); *C07C 2523/44* (2013.01); *C07C 2529/08* (2013.01); *C07C 2529/18* (2013.01); *C07C 2529/70* (2013.01); *C07C 2529/74* (2013.01); *C07C 2601/14* (2017.05)

(58) Field of Classification Search
  CPC .. C07C 13/28; C07C 2/74; C07C 5/10; C07C 5/367; C07C 6/126; C07C 15/14; C07C 2523/42; C07C 2523/44; C07C 2529/08; C07C 2529/18; C07C 2529/70; C07C 2529/74; C07C 2601/14; C07C 5/11
  See application file for complete search history.

(56) References Cited

U.S. PATENT DOCUMENTS

| | | |
|---|---|---|
| 2,520,084 A | 8/1950 | Dazzi |
| 2,634,248 A | 4/1953 | Dazzi |
| 2,976,266 A | 3/1961 | Lytton et al. |
| 3,296,065 A | 1/1967 | O'Brien et al. |
| 3,842,040 A | 10/1974 | Browne et al. |
| 3,842,041 A | 10/1974 | Browne et al. |
| 3,928,481 A | 12/1975 | Suggitt |
| 3,928,484 A | 12/1975 | Suggitt |
| 3,962,362 A | 6/1976 | Suggitt |
| 4,123,470 A | 10/1978 | Murtha |
| 4,218,572 A | 8/1980 | Dolhyj et al. |
| 4,263,457 A | 4/1981 | Takeda et al. |
| 4,294,976 A | 10/1981 | Itatani et al. |
| 4,463,207 A | 7/1984 | Johnson |
| 4,959,450 A | 9/1990 | Morris et al. |
| 5,001,296 A | 3/1991 | Howley et al. |
| 5,138,022 A | 8/1992 | Mang et al. |

(Continued)

FOREIGN PATENT DOCUMENTS

| | | |
|---|---|---|
| JP | 03-106833 | 5/1991 |
| JP | 07-173086 | 7/1995 |

(Continued)

OTHER PUBLICATIONS

U.S. Appl. No. 61/577,900, filed Dec. 20, 2011, Dakka et al.
U.S. Appl. No. 62/012,024, filed Jun. 13, 2014, Salciccioli et al.
U.S. Appl. No. 62/012,037, filed Jun. 13, 2014, Dakka et al.
U.S. Appl. No. 62/026,889, filed Jan. 27, 2015, Dakka et al.
U.S. Appl. No. 62/068,144, filed Oct. 24, 2014, Dakka et al.
U.S. Appl. No. 62/094,218, filed Dec. 19, 2014, Salciccioli et al.

(Continued)

*Primary Examiner* — Sharon Pregler

(57) ABSTRACT

In a process for producing dialkylbiphenyl compounds, a feed comprising substituted cyclohexylbenzene isomers having the formula (I):

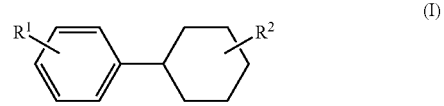

wherein each of $R^1$ and $R^2$ is an alkyl group and wherein the feed comprises m % by weight of isomers in which $R^1$ is in the 2-position, based on the total weight of substituted cyclohexylbenzene isomers in the feed; is transalkylated with a compound of formula (II):

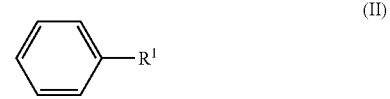

to produce a transalkylation product comprising substituted cyclohexylbenzene isomers having the formula (I) and including n % by weight of isomers in which $R^1$ is in the 2-position, based on the total weight of substituted cyclohexylbenzene isomers in the transalkylation product, wherein n<m. At least part of the transalkylation product is then dehydrogenated under conditions effective to convert at least part of the substituted cyclohexylbenzene isomers in the transalkylation product to dialkylbiphenyl compounds.

26 Claims, 3 Drawing Sheets

(56) References Cited

U.S. PATENT DOCUMENTS

| | | | |
|---|---|---|---|
| 6,037,513 A | 3/2000 | Chang et al. | |
| 6,103,919 A | 8/2000 | Schiraldi et al. | |
| 6,274,756 B1 | 8/2001 | Caers et al. | |
| 6,355,711 B1 | 3/2002 | Godwin et al. | |
| 6,433,236 B1 | 8/2002 | Schiraldi et al. | |
| 6,482,972 B1 | 11/2002 | Bahrmann et al. | |
| 6,730,625 B1 | 5/2004 | Chang et al. | |
| 6,740,254 B2 | 5/2004 | Zhou et al. | |
| 6,777,514 B2 | 8/2004 | Patil et al. | |
| 7,297,738 B2 | 11/2007 | Gosse et al. | |
| 8,829,093 B2 | 9/2014 | Dakka et al. | |
| 2005/0137437 A1 | 6/2005 | Soloveichik et al. | |
| 2005/0215433 A1 | 9/2005 | Benitez et al. | |
| 2006/0247461 A1 | 11/2006 | Schlosberg et al. | |
| 2008/0242895 A1 | 10/2008 | Godwin et al. | |
| 2009/0299111 A1 | 12/2009 | Kanbara et al. | |
| 2010/0159177 A1 | 6/2010 | Dakka et al. | |
| 2011/0151162 A1 | 6/2011 | Dakka et al. | |
| 2011/0184105 A1 | 7/2011 | Dakka et al. | |
| 2011/0215433 A1 | 9/2011 | Kokubum | |
| 2012/0108726 A1 | 5/2012 | Godwin et al. | |
| 2012/0108874 A1 | 5/2012 | Gralla et al. | |
| 2012/0283494 A1 | 11/2012 | Smith et al. | |
| 2014/0212666 A1 | 7/2014 | Dakka et al. | |
| 2014/0272626 A1 | 9/2014 | Berlowitz et al. | |
| 2014/0275605 A1 | 9/2014 | Dakka et al. | |
| 2014/0275606 A1 | 9/2014 | Bai et al. | |
| 2014/0275607 A1 | 9/2014 | Dakka et al. | |
| 2014/0275609 A1 | 9/2014 | Dakka et al. | |
| 2014/0315021 A1 | 10/2014 | Naert et al. | |
| 2014/0316155 A1 | 10/2014 | Dakka et al. | |
| 2014/0323782 A1 | 10/2014 | Chen et al. | |
| 2014/0378697 A1* | 12/2014 | de Smit | B01J 29/12 585/252 |
| 2015/0080545 A1 | 3/2015 | Dakka et al. | |
| 2015/0080546 A1 | 3/2015 | Dakka et al. | |

FOREIGN PATENT DOCUMENTS

| | | |
|---|---|---|
| JP | 08-020548 | 1/1996 |
| JP | 08-099914 | 4/1996 |
| SU | 412182 | 1/1974 |
| WO | WO 99/32427 | 7/1999 |
| WO | WO 2003/029339 | 4/2003 |
| WO | WO 2004/046078 | 6/2004 |
| WO | WO 2007/013469 | 2/2007 |
| WO | WO 2010/138248 | 12/2010 |
| WO | WO 2011/096989 | 8/2011 |
| WO | WO 2011/096993 | 8/2011 |
| WO | WO 2012/082407 | 6/2012 |
| WO | WO 2014/159094 | 10/2014 |
| WO | WO 2014/159104 | 10/2014 |

OTHER PUBLICATIONS

U.S. Appl. No. 62/137,996, filed Mar. 25, 2015, Salciccioli et al.
U.S. Appl. No. 62/138,179, filed Mar. 25, 2015, Evans et al.
U.S. Appl. No. 62/140,723, filed Mar. 31, 2015, Salciccioli et al.
U.S. Appl. No. 14/164,889, filed Jan. 27, 2013, Dakka et al.
U.S. Appl. No. 14/201,224, filed Mar. 7, 2014, Dakka et al.
U.S. Appl. No. 14/201,226, filed Mar. 7, 2014, Bai et al.
U.S. Appl. No. 14/201,284, filed Mar. 7, 2014, Dakka et al.
U.S. Appl. No. 14/201,287, filed Mar. 7, 2014, Dakka et al.
U.S. Appl. No. 14/516,239, filed Oct. 16, 2014, Dakka et al.
Bandyopadhyay et al., "Transalkylation of cumene with toluene over zeolite Beta," Applied Catalysis A: General, vol. 135(2), (1996), pp. 249-259.
Bandyopadhyay et al., "Transalkylation reaction ± An alternative route to produce industrially important intermediates such as cymene," Catalysis Today, 44, (1998) pp. 245-252.
Lu et al., "Selective Hydrogenation of Single Benzene Ring in Biphenyl Catalyzed by Skeletal Ni," ChemCatChem., vol. 1(3), (2009) pp. 369-371.

U.S. Appl. No. 14/723,546, filed May 28, 2015.
U.S. Appl. No. 13/316,745, filed Dec. 12, 2011, Patil et al.
U.S. Appl. No. 14/201,173, filed Mar. 7, 2014, Dakka et al.
U.S. Appl. No. 14/480,363, filed Sep. 8, 2014, Dakka et al.
U.S. Appl. No. 14/486,945, filed Sep. 15, 2014, Dobin et al.
U.S. Appl. No. 14/527,480, filed Oct. 29, 2014, Patil et al.
U.S. Appl. No. 61/040,480, filed Mar. 28, 2008, Godwin.
U.S. Appl. No. 61/203,626, filed Dec. 24, 2008, Dakka et al.
U.S. Appl. No. 61/781,109, filed Mar. 14, 2013, Dakka et al.
U.S. Appl. No. 61/781,116, filed Mar. 14, 2014, Bai et al.
U.S. Appl. No. 61/781,129, filed Mar. 14, 2014, Dakka et al.
U.S. Appl. No. 61/781,137, filed Mar. 14, 2014, Dakka et al.
U.S. Appl. No. 61/781,728, filed Mar. 14, 2014, Dakka et al.
U.S. Appl. No. 62/026,889, filed Jul. 21, 2014, Mohr et al.
Borodina et al., "Hydroalkylation of Benzene and Ethylbenzene over Metal-Containing Zeolite Catalysts," Petroleum Chemistry, 2009, vol. 49(1), pp. 66-73.
Clary et al., "A Green, One-Pot Route to the Biphenyldicarboxylic Acids: Useful Intermediates in Polymer Synthesis," International Journal of Organic Chemistry, Jun. 2013, vol. 3(2), pp. 143-147.
Ennis et al., "Multikilogram-Scale Synthesis of a Biphenyl Carboxylic Acid Derivative Using a Pd/C-Mediated Suzuki Coupling Approach," Organic Process R&D, 1999, vol. 3(4), pp. 248-252.
Godwin, et al., "Plasticizers," Applied Polymer Science: $21^{st}$ Century, Elsevier, 2000, pp. 157-175.
Guo et al., "Reactivity of 4,4'-Dimethylbiphenyl with Methanol over modified HZSM-5 Catalysts," PrePrints—American Chemical Society, Division of Petroleum Chemistry, 2003, vol. 48(4), pp. 280-282.
Hoefnagel et al., "Selective alkylation of methylbenzenes with cyclohexene catalyzed by solid acids," Catalysis Letters, vol. 85, No. 1-2, 2003, pp. 7-11.
Izard, "Effect of Chemical Structure on Physical Properties of Isomeric Polyesters," Journal of Polymer Science, 1952, vol. 9(1), 35-39.
Khromov et al., "Catalytic Conversion of 1,1'-Dimethyldicyclohexyl and 1-Methyl-1-Phenyl-Cyclohexane on Platinum Catalysts at Elevated Hydrogen Pressures and Temperatures,"Vestnik Moskovskogo Universiteta, Seriya 2: Khimiya (1965), 20(1), 51-5, (English AbstractOnly).
Krigbaum et al., "Aromatic Polyesters Forming Thermotropic Smectic Mesophases," Journal of Polymer Science, Part C, Polymer Letters Edition, 1982, vol. 20(2), pp. 109-115.
Kulev et al., "Esters of diphenic acid and their plasticizing properties," Izvestiya Tomskogo Politekhnicheskogo Instituta, 1961, vol. 111 (Abstract).
Lagidze et al., "Analysis of Substances Produced by Reaction Between Aluminum Chloride and Diphenyl in Dearotnatized Ligroin," V.I. Leni-n Georgian Polytechnic Institute (1968), No. 2 (122), pp. 36-44. (English Translation).
Mavrodinova et al., "Transalkylation of toluene with cumene over zeolites Y dealuminated in solid-state, Part I. Effect of the alteration of Broensted acidity," Applied Catalysis A:General, 2003,vol. 248, pp. 181-196.
Mavrodinova et al., "Transalkylation of toluene with cumene over zeolites Y dealuminated in solid-state Part II. Effect of the introduced Lewis acid sites," Applied Catalysis A: General, 2003, vol. 248, p. 197-209.
Meurisse et al., "Polymers with Mesogenic Elements and Flexible Spacers in the Main Chain: Aromatic-Aliphatic Polyesters," British Polymer Journal, 1981, vol. 13(2), pp. 55-63.
Mukhopadhyay et al., "Tandem One-Pot Palladium-Catalyzed Reductive and Oxidative Coupling of Benzene and Chlorobenzene," Journal of Organic Chemistry, 2000, vol. 65(10), pp. 3107-3110.
Roux et al., "Critically Evaluated Thermochemical Properties of Polycyclic Aromatic Hydrocarbons," Journal of Physical and Chemical Reference Data, 2008, vol. 37(4), pp. 1855-1996.
Sherman et al., "Dimethylbiphenyls from toluene," American Chemical Society, Chemical Innovation, 2000, pp. 25-30.
Shioda et al., "Synthesis of dialkyl diphenates and their properties," Yuki Gosei Kagaku Kyokaishi 1959, 17.

(56) References Cited

OTHER PUBLICATIONS

Sinfelt, "The turnover frequency of methylcyclohexane dehydrogenation to toluene on a Pt reforming catalyst," Journal of Molecular Catalysis A: Chemical, 2000, vol. 163, pp. 123-128.

Sinfelt et al., "Kinetics of Methylcyclohexane Dehydrogenation Over PT-$Al_2O_3$," Journal of Physical Chemistry, 1960, vol. 64(10), 1559-1562.

Singh, et. al, *Studies on Isomer Distribution in the Products Obtained by Friedelcrafts Alkylation of Toulene with Cyclic Electrophiles*," National Academy Science Letters, 1983, vol. 6(10), pp. 321-325.

Zhang, et al., "Automation of Fluorous Solid-Phase Extraction for Parallel Synthesis," J. Comb. Chem, 2006, vol. 8, pp. 890-896.

\* cited by examiner

PROCESS FOR PREPARING DIALKYLBIPHENYL ISOMER MIXTURES

PRIORITY

This invention claims priority to and the benefit of U.S. Ser. No. 62/012,024, filed Jun. 13, 2014.

FIELD OF THE INVENTION

This invention relates to a process for preparing a mixture of dialkylbiphenyl isomers, particularly a mixture of dimethylbiphenyl isomers having an increased concentration of the 3,3', 3,4', and 4,4' isomers.

BACKGROUND OF THE INVENTION

Dimethylbiphenyl (DMBP) and other dialkylbiphenyls are useful intermediates in the production of a variety of commercially valuable products, including polyesters and plasticizers for PVC and other polymer compositions. For example, DMBP can readily be converted to an ester plasticizer by a process comprising oxidation of the DMBP to produce the corresponding mono- or dicarboxylic acid followed by esterification with a long chain alcohol. However, for certain uses, it is important to reduce the level of 2,X' DMBP (where X' is 2', 3' and 4') isomers in the product since, for example, diphenate esters having substitution on the 2-carbons tend to be too volatile for use as plasticizers.

As disclosed in our co-pending U.S. Ser. Nos. 14/201,287 and 14/201,224, both filed Mar. 7, 2014, dimethylbiphenyl may be produced by hydroalkylation of toluene followed by dehydrogenation of the resulting (methylcyclohexyl)toluene (MCHT). However, even using a selective molecular sieve catalyst for the hydroalkylation step, this process tends to yield a mixture of all six DMBP isomers, namely 2,2', 2,3' 2,4', 3,3', 3,4' and 4,4' DMBP, in which the 2,X' DMBP isomer content may be 20% by weight or more of the total DMBP product. Moreover, 2,2', 2,3' and 2,4' DMBP cannot be completely separated from unreacted MCHT by distillation due to an overlap in their vapor-liquid equilibrium properties. There is, therefore, interest in developing a process for converting 2,X' DMBP isomers into 3,3', 3,4' and 4,4' DMBP and especially a process which effects such a conversion with minimal loss of any unconverted MCHT which may be present in the DMBP feed.

The production of biphenylesters is based on the initial steps of aromatic hydroalkylation (see U.S. Ser. No. 14/201,226, U.S. Ser. No. 14/201,287, and U.S. Ser. No. 14/201,224, filed Mar. 7, 2013), followed by dehydrogenation to produce biphenyls or alkylbiphenyls (see U.S. Ser. No. 14/164,889, filed Jan. 27, 2013, U.S. Ser. No. 14/201,287, and U.S. Ser. No. 14/201,284, filed Mar. 7, 2013).

SUMMARY OF THE INVENTION

According to the present invention, it has now been found that the amount of 2,X' DMBP isomers in a DMBP isomer mixture can be reduced by a combination of hydrogenation of the DMBP back to MCHT, followed by transalkylation of the MCHT with toluene and then dehydrogenation of the transalkylation product back to DMBP. In particular, it is found that steric issues favor the transalkylation of 1-methyl-2-(X-methylcyclohexyl)benzene (where X=2, 3 or 4) with toluene to produce 1-methyl-Y—(X-methylcyclohexyl)benzene (where Y=3 or 4 and X is the same position as the feed).

In one aspect, the invention resides in a process for producing dialkylbiphenyl compounds, the process comprising:

(a1) providing a feed comprising substituted cyclohexylbenzene isomers having the formula (I):

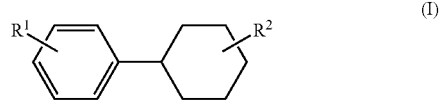

wherein each of $R^1$ and $R^2$ is an alkyl group and wherein the feed comprises m % by weight of isomers in which $R^1$ is in the 2-position, based on the total weight of substituted cyclohexylbenzene isomers in the feed;

(a2) reacting the feed under transalkylation conditions with a compound of formula (II):

wherein $R^{1*}$ is an alkyl group, to produce a transalkylation product comprising substituted cyclohexylbenzene isomers having the formula (I) and including n % by weight of isomers in which $R^1$ is in the 2-position, based on the total weight of substituted cyclohexylbenzene isomers in the transalkylation product, wherein n<m; and (a3) dehydrogenating at least part of the transalkylation product under conditions effective to convert at least part of the substituted cyclohexylbenzene isomers in the transalkylation product to dialkylbiphenyl compounds.

In a further aspect, the invention resides in a process for reducing the amount of 2,X' dialkylbiphenyl isomers (where X' is 2', 3' and/or 4') in a first mixture containing the same, the process comprising:

(b1) hydrogenating the first mixture under conditions effective to produce a hydrogenation product comprising substituted cyclohexylbenzene isomers having the formula (I):

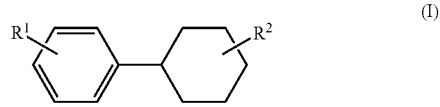

wherein each of $R^1$ and $R^2$ is an alkyl group and wherein the hydrogenation product comprises m % by weight of isomers in which $R^1$ is in the 2-position, based on the total weight of substituted cyclohexylbenzene isomers in the hydrogenation product;

(b2) reacting the hydrogenation product under transalkylation conditions with a compound of formula (II):

where $R^{1*}$ is an alkyl group, to produce a transalkylation product comprising substituted cyclohexylbenzene isomers having the formula (I) and including n % by weight of isomers in which $R^1$ is in the 2-position, based on the total weight of substituted cyclohexylbenzene isomers in the transalkylation product, wherein n<m; and (b3) dehydrogenating at least part of the substituted cyclohexylbenzene isomers in the transalkylation product to produce a product mixture containing less 2,3' and 2,4' dialkylbiphenyl isomers than the first mixture.

In yet a further aspect, the invention resides in a process for producing dimethylbiphenyl compounds, the process comprising:

(c1) contacting toluene with hydrogen under hydroalkylation conditions effective to produce a hydroalkylation product comprising (methylcyclohexyl)toluenes;

(c2) dehydrogenating at least part of the hydroalkylation product under conditions effective to produce a first dehydrogenation product comprising dimethylbiphenyl isomers and unreacted (methylcyclohexyl)toluenes;

(c3) separating the first dehydrogenation product into a first fraction comprising one or more 3,3', 3,4' and 4,4' dimethylbiphenyl isomers and a second fraction comprising one or more 2,X'-dimethylbiphenyl isomers (where X' is 2, 3 or 4) and at least part of the unreacted (methylcyclohexyl) toluenes;

(c4) hydrogenating at least part of the dimethylbiphenyl isomers in the second fraction to the corresponding (methylcyclohexyl)toluene isomers and produce a hydrogenation effluent;

(c5) reacting at least part of the hydrogenation effluent from (c4) with toluene under transalkylation conditions effective to produce a transalkylation product containing less material represented by Formula (X) than the hydrogenation effluent, where Formula (X) is

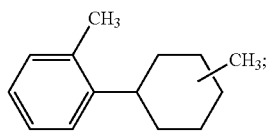

and (c6) dehydrogenating at least part of the transalkylation product to produce a second dehydrogenation product comprising less 2,X'-dimethylbiphenyl isomers than the first dehydrogenation product.

DETAILED DESCRIPTION OF THE EMBODIMENTS

Figure 1:
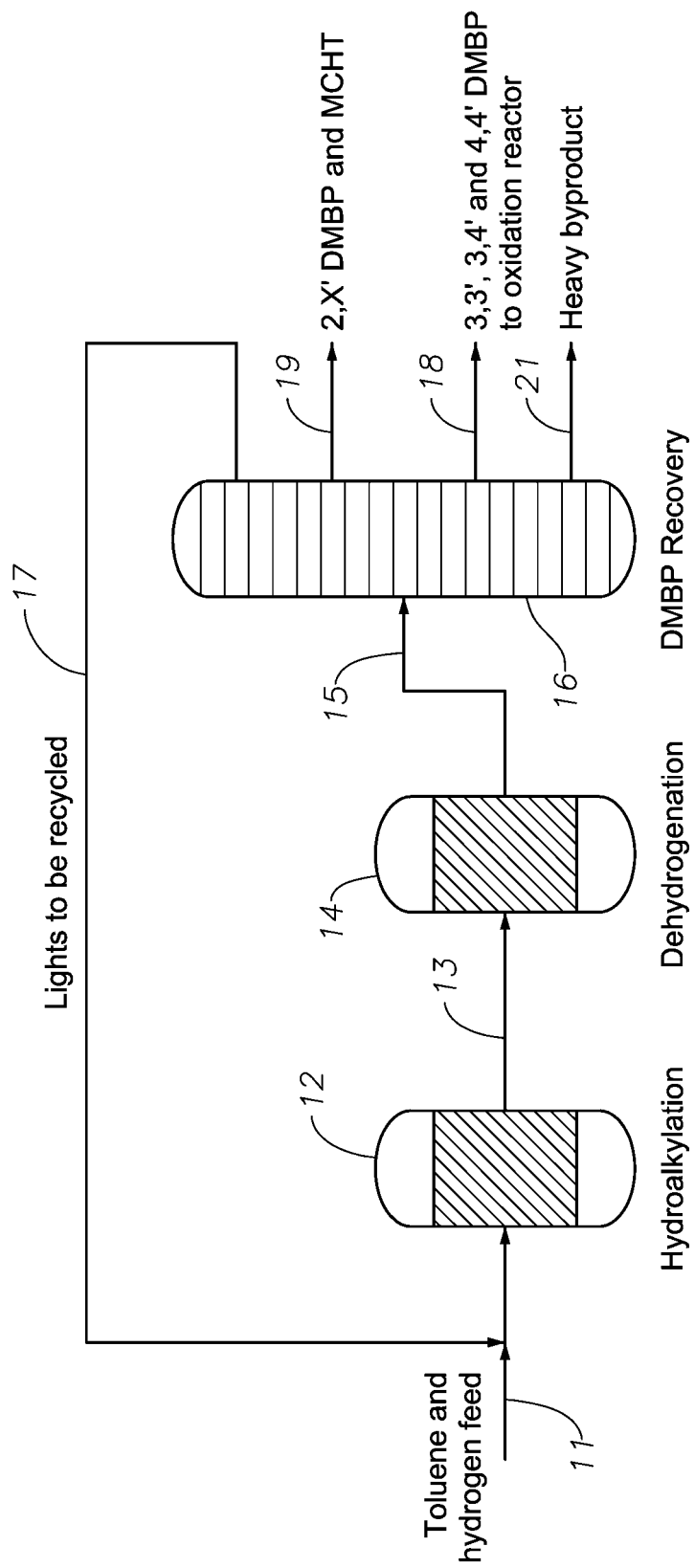
FIG. 1 is a flow diagram of a process for producing a mixture of dimethylbiphenyl isomers according to one embodiment of the invention.

Described herein is a process for producing dialkylbiphenyl compounds useful as precursors in the manufacture of polyesters and biphenyl ester plasticizers. In particular, the present process provides a route for the production of a mixture of dialkylbiphenyl isomers in which the amount of the 3,3', 3,4' and 4,4'-dialkylbiphenyl isomerizers is maximized and the amount of the 2,X' dialkylbiphenyl isomers (where X' is 2', 3' and/or 4') is minimized.

By way of illustration, the 3,3', 3,4' and 4,4'-isomers of dimethylbiphenyl are shown below in formulas (III) to (V) respectively, whereas the 2,2', 2,3' and 2,4'-isomers are shown in formulas (VI) to (VIII) respectively:

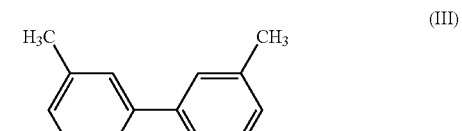

(III)

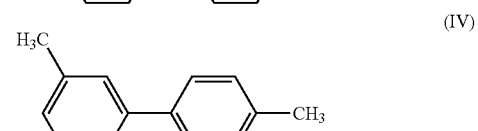

(IV)

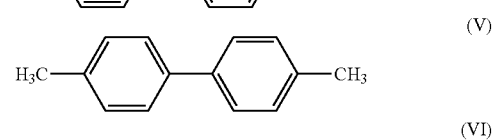

(V)

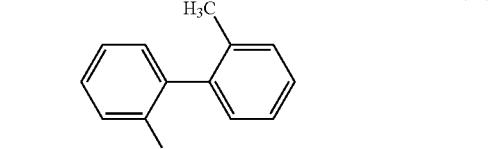

(VI)

(VII)

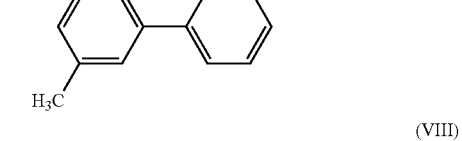

(VIII)

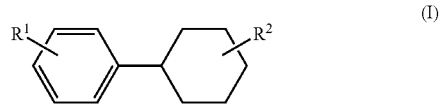

In its simplest form, the present process starts with a feed comprising a first mixture of substituted cyclohexylbenzene isomers having the formula (I):

(I)

wherein each of $R^1$ and $R^2$ is an alkyl group and wherein the feed comprises m % by weight of isomers in which $R^1$ is in the 2-position, based on the total weight of substituted cyclohexylbenzene isomers in the feed. The number of carbon atoms in each alkyl group can be the same or different, but in most embodiments will be the same and will be less than 10, such as from 1 to 5. Normal alkyl groups are preferred and most preferably each of $R^1$ and $R^2$ is a methyl group.

In the present process, the feed comprising the mixture of substituted cyclohexylbenzene isomers having the formula (I) is initially transalkylated with a compound of formula (II):

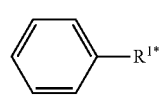
(II)

where $R^{1*}$ is an alkyl group (preferably having 1 to 10 carbon atoms, preferably 1 to 5 carbon atoms, preferably $R^{1*}$ is methyl), to produce a transalkylation product comprising a second mixture of substituted cyclohexylbenzene isomers having the formula (I) and including n % by weight of isomers in which $R^1$ is in the 2-position, based on the total weight of substituted cyclohexylbenzene isomers in the transalkylation product. As a result of steric issues, it is found that the transalkylation favors the production of the cyclohexylbenzene isomers in which the $R^1$ group is in the 3-position or the 4-position so that n<m. The discrete values for m and n can vary widely depending on the process used to produce the first mixture substituted cyclohexylbenzene isomers and the conditions and catalyst employed in the transalkylation step. However, in certain embodiments, m is at least 1%, such as at least 15%, for example, from 15% to 30% and n is less than 99%, such as less than 60%, for example from 1% to 15%. In an alternate embodiment, m is at least 5 wt % and n is less than 75 wt %.

The transalkylation reaction can be conducted over a wide range of conditions but in most embodiments is effected at a temperature from 75° C. to 250° C., such as from 100° C. to 200° C., for example, 125° C. to 160° C. and a pressure from 100 to 3550 kPa-absolute, such as from 1000 to 1500 kPa-absolute. The reaction is normally conducted in the presence of a solid acid catalyst, such as a molecular sieve and in particular a molecular sieve having a large pore molecular sieve having a Constraint Index (as defined in U.S. Pat. No. 4,016,218) less than 2. Suitable large pore molecular sieves include zeolite beta, zeolite Y, Ultrastable Y (USY), Dealuminized Y (Deal Y), mordenite, ZSM-3, ZSM-4, ZSM-18, ZSM-20, and mixtures thereof. Other suitable molecular sieves include molecular sieves of the MCM-22 family, including MCM-22 (described in U.S. Pat. No. 4,954,325), PSH-3 (described in U.S. Pat. No. 4,439,409), SSZ-25 (described in U.S. Pat. No. 4,826,667), ERB-1 (described in EP 0293032), ITQ-1 (described in U.S. Pat. No. 6,077,498), ITQ-2 (described in WO 97/17290), MCM-36 (described in U.S. Pat. No. 5,250,277), MCM-49 (described in U.S. Pat. No. 5,236,575), MCM-56 (described in U.S. Pat. No. 5,362,697) and mixtures thereof.

According to the present process, at least part of the transalkylation product is then catalytically dehydrogenated to produce the desired mixture of dialkylbiphenyl isomers. The catalyst employed in the dehydrogenation process is not critical but, in some embodiments, comprises (i) an element or compound thereof from Group 10 of the Periodic Table of Elements, for example platinum, and (ii) tin or a compound of tin, both mounted on a refractory support, such as silica, alumina or carbon nanotubes. Suitable catalysts comprise a Group 10 element in an amount from 0.1 to 5 wt % of the catalyst and tin in an amount from 0.05 to 2.5 wt % of the catalyst. The dehydrogenation is conveniently conducted at a temperature from about 200° C. to about 600° C. and a pressure from about 100 kPa-absolute to about 3550 kPa-absolute (atmospheric to about 500 psig).

The amount of 2,X' isomers in the resultant mixture of dialkylbiphenyl isomers will of course depend on the value of n in the substituted cyclohexylbenzene isomers produced by the transalkylation step and the level of conversion of each MCHT isomer in the dehydrogenation step. However, in representative embodiments, the dehydrogenation product contains less than 30%, for example from 10 to 25% of 2,X'-dialkylbiphenyl isomers based on the total weight of dialkylbiphenyl compounds in the dehydrogenation product.

Although any known method can be used to produce the mixture of substituted cyclohexylbenzene isomers having the formula (I) employed as the feed in the above-described process, in one embodiment the feed is produced by hydrogenation of a precursor mixture of dialkylbiphenyl isomers. In this case, the overall process can be summarized as follows:

(i) Hydrogenation of a precursor dialkylbiphenyl isomer mixture to produce a first mixture of substituted cyclohexylbenzene isomers having the formula (I).
(ii) Transalkylation of the product of (i) with a compound of formula (II) to produce a second mixture of substituted cyclohexylbenzene isomers having a different isomer distribution than the first mixture.
(iii) Dehydrogenation of the product of (ii) to produce a further dialkylbiphenyl isomer mixture having a different isomer distribution than the precursor mixture.

In the above embodiment, the present process effectively provides a three-step method of isomerizing a mixture of dialkylbiphenyl isomers so as to reduce the level of 2,X' isomers in the mixture.

In one preferred embodiment, where each of $R^1$ and $R^2$ in formula (I) is a methyl group, the present process forms part of the product recovery system of an integrated process for selectively converting toluene to 3,3', 3,4' and 4,4' dimethylbiphenyl. In such a process, toluene is initially converted to (methylcyclohexyl)toluenes over a hydroalkylation catalyst according to the following reaction:

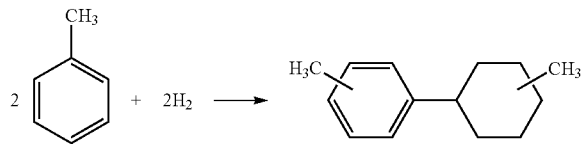

The catalyst employed in the hydroalkylation reaction is a bifunctional catalyst comprising a hydrogenation component and a solid acid alkylation component, typically a molecular sieve. The catalyst may also include a binder such as clay, alumina, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Any known hydrogenation metal or compound thereof can be employed as the hydrogenation component of the catalyst, although suitable metals include palladium, ruthenium, nickel, zinc, tin, and cobalt, with palladium being particularly advantageous. In certain embodiments, the amount of hydrogenation metal present in the catalyst is between about 0.05 and about 10 wt %, such as between about 0.1 and about 5 wt %, of the catalyst. In an embodiment, the hydrogenation catalyst (used in step (b1)) is a transition metal, preferably a Group 3, 4, 5, 6, 7, 8, 9, 10, 11, or 12 metal, preferably Ru, Rh, Pd, Ag, Os, Ir, Pt, A, or preferably Pt or Pd.

In one embodiment, the solid acid alkylation component comprises a large pore molecular sieve having a Constraint Index (as defined in U.S. Pat. No. 4,016,218) less than 2. Suitable large pore molecular sieves include zeolite beta, zeolite Y, Ultrastable Y (USY), Dealuminized Y (Deal Y), mordenite, ZSM-3, ZSM-4, ZSM-18, and ZSM-20. Zeolite ZSM-4 is described in U.S. Pat. No. 4,021,447. Zeolite ZSM-20 is described in U.S. Pat. No. 3,972,983. Zeolite Beta is described in U.S. Pat. No. 3,308,069, and Re. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104.

In another more preferred embodiment, the solid acid alkylation component comprises a molecular sieve of the MCM-22 family. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in EP 0293032), ITQ-1 (described in U.S. Pat. No. 6,077,498), ITQ-2 (described in WO 97/17290), MCM-36 (described in U.S. Pat. No. 5,250,277), MCM-49 (described in U.S. Pat. No. 5,236,575), MCM-56 (described in U.S. Pat. No. 5,362,697) and mixtures thereof.

In addition to the toluene, benzene and/or xylene and hydrogen, a diluent, which is substantially inert under hydroalkylation conditions, may be included in the feed to the hydroalkylation reaction. In certain embodiments, the diluent is a hydrocarbon, in which the desired cycloalkylaromatic product is soluble, such as a straight chain paraffinic hydrocarbon, a branched chain paraffinic hydrocarbon, and/or a cyclic paraffinic hydrocarbon. Examples of suitable diluents are decane and cyclohexane. Although the amount of diluent is not narrowly defined, desirably the diluent is added in an amount such that the weight ratio of the diluent to the aromatic compound is at least 1:100; for example at least 1:10, but no more than 10:1, desirably no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 and about 7,000 kPa, such as between about 500 and about 5,000 kPa. The molar ratio of hydrogen to aromatic feed is typically from about 0.15:1 to about 15:1.

In the present process, it is found that MCM-22 family molecular sieves are particularly active and stable catalysts for the hydroalkylation of toluene or xylene. In addition, catalysts containing MCM-22 family molecular sieves exhibit improved selectivity to the 3,3'-dimethyl, the 3,4'-dimethyl, the 4,3'-dimethyl and the 4,4'-dimethyl isomers in the hydroalkylation product, while at the same time reducing the formation of fully saturated and heavy by-products. For example, using an MCM-22 family molecular sieve with a toluene feed, it is found that the hydroalkylation reaction product may comprise:

at least 60 wt %, such as at least 70 wt %, for example at least 80 wt % of the 3,3', 3,4', 4,3' and 4,4'-isomers of (methylcyclohexyl)toluene based on the total weight of all the (methylcyclohexyl)toluene isomers;

less than 40 wt %, such as less than 30 wt %, for example from 15 to 25 wt % of the 2,2', 2,3', and 2,4'-isomers of (methylcyclohexyl)toluene based on the total weight of all the (methylcyclohexyl)toluene isomers;

less than 30 wt % of methylcyclohexane and less than 2% of dimethylbicyclohexane compounds; and less than 1 wt % of compounds containing in excess of 14 carbon atoms.

The hydroalkylation reaction product may also contain significant amounts of residual toluene, for example, up to 50 wt %, such as up to 90 wt %, typically from 60 to 80 wt % of residual toluene based on the total weight of the hydroalkylation reaction product. Thus, the major components of the hydroalkylation reaction effluent are (methylcyclohexyl)toluenes, residual toluene and fully saturated single ring by-product (methylcyclohexane). The residual toluene and light by-products can readily be removed from the reaction effluent by, for example, distillation. The residual toluene can then be recycled to the hydroalkylation reactor, while the saturated by-products can be dehydrogenated to produce additional recyclable feed.

The remainder of the hydroalkylation reaction effluent, composed mainly of (methylcyclohexyl)toluenes, is then dehydrogenated to convert the (methylcyclohexyl)toluenes to the corresponding methyl-substituted biphenyl compounds. The dehydrogenation is conveniently conducted at a temperature from about 200° C. to about 600° C. and a pressure from about 100 kPa to about 3550 kPa (atmospheric to about 500 psig) in the presence of dehydrogenation catalyst. A suitable dehydrogenation catalyst comprises one or more elements or compounds thereof selected from Group 10 of the Periodic Table of Elements, for example platinum, on a support, such as silica, alumina or carbon nanotubes. In one embodiment, the Group 10 element is present in amounts from 0.1 to 5 wt % of the catalyst. In some cases, the dehydrogenation catalyst may also include tin or a tin compound to improve the selectivity to the desired methyl-substituted biphenyl product. In one embodiment, the tin is present in amounts from 0.05 to 2.5 wt % of the catalyst.

Particularly using an MCM-22 family-based catalyst for the upstream hydroalkylation reaction, the product of the dehydrogenation step comprises dimethylbiphenyl compounds in which the concentration of the 3,3'-, 3,4'- and 4,4' isomers is at least 50 wt %, such as at least 60 wt %, for example at least 70 wt % based on the total weight of dimethylbiphenyl compounds. Typically, the concentration of the 2,X'-dimethylbiphenyl isomers in the dehydrogenation product is less than 50 wt %, such as less than 30 wt %, for example from 5 to 25 wt % based on the total weight of dimethylbiphenyl compounds.

By virtue of their higher boiling point, the 3,3'-, 3,4'- and 4,4'-dimethylbiphenyl isomers can readily be separated from the hydrogenation product by distillation, but 2,2', 2,3' and 2,4' isomers cannot be completely separated from residual (methylcyclohexyl)toluenes by distillation due to an overlap in their vapor-liquid equilibrium properties. In the present process, this problem is alleviated in that, after recovery of at least some of the 3,3'-, 3,4'- and 4,4' isomers, part or all of the remaining dehydrogenation product is subjected to the three-step "isomerization" process, described above, namely hydrogenation, followed by transalkylation followed by dehydrogenation, to convert at least some of 2,X' isomers to their 3,3'-, 3,4'- and 4,4'-counterparts. This process can be repeated effectively to convert all the 2,X'-dimethylbiphenyl compounds to their more desirable 3,3'-, 3,4'- and 4,4' isomers. In addition, it is found that the loss in dimethylbiphenyl yield through conversion to unwanted by-products during the three-step "isomerization" process is very low thereby enhancing the overall selectivity and yield of the integrated process for converting toluene to 3,3'-, 3,4'- and 4,4'-dimethylbiphenyl compounds.

One embodiment of such an integrated process is illustrated in FIG. 1, in which toluene and hydrogen are fed by a single line 11 or, if preferred by separate lines (not shown), to a hydroalkylation unit 12. The hydroalkylation unit 12 contains a bed of a bifunctional catalyst which comprises a hydrogenation component and a solid acid alkylation component and which converts the toluene to (methylcyclohexyl)toluene (MCHT). The effluent from the hydroalkylation unit 12, composed mainly of MCHT and unreacted toluene, is then fed via line 13 to a dehydrogenation unit 14 where the MCHT is dehydrogenated to produce dimethyldiphenyl (DMBP) and hydrogen. If preferred, distillation or other separation techniques can be implemented to concentrate the MCHT or remove hydroalkylation byproducts prior to the dehydrogenation step (stream 13).

The effluent from the dehydrogenation unit 14 is then supplied by line 15 to a DMBP recovery system 16, including one or more distillation columns, where hydrogen and unreacted toluene are removed as overhead and recycled via line 17 to the hydroalkylation unit 12. Also removed from the dehydrogenation effluent by DMBP recovery system 16 are a first intermediate stream rich in 3,3'-, 3,4'- and 4,4'-DMBP isomers, which is recovered as product via line 18, and a second intermediate stream rich in 2,X'-DMBP isomers and residual MCHT, which is removed via line 19. Heavies in the dehydrogenation effluent containing, for example, $C_{21}+$ compounds from polyalkylation reactions occurring in the hydroalkylation unit 12 or methylfluorene byproduct from the dehydrogenation reactions, are collected in line 21 and recovered for use as fuel or as feedstock to other chemical processes.

Although not shown in FIG. 1, the second intermediate stream, rich in 2,X'-DMBP isomers and residual MCHT, is supplied by line 19 to a separate isomerization section comprising a hydrogenation unit, then a transalkylation unit and finally a second dehydrogenation unit. As discussed above, the hydrogenation unit converts the 2,X'-DMBP isomers back to the corresponding MCHT isomers, then the transalkylation unit reacts the MCHT (both converted from, and residual in, the second intermediate stream) with toluene to produce a transalkylation product having a different MCHT isomer distribution that the second intermediate stream. The second dehydrogenation unit then converts the MCHT in the transalkylation product to DMBP having a different isomer distribution than that in line 15. In some embodiments, the hydrogenation unit and the transalkylation unit can be combined as a single reactor.

Figure 2:
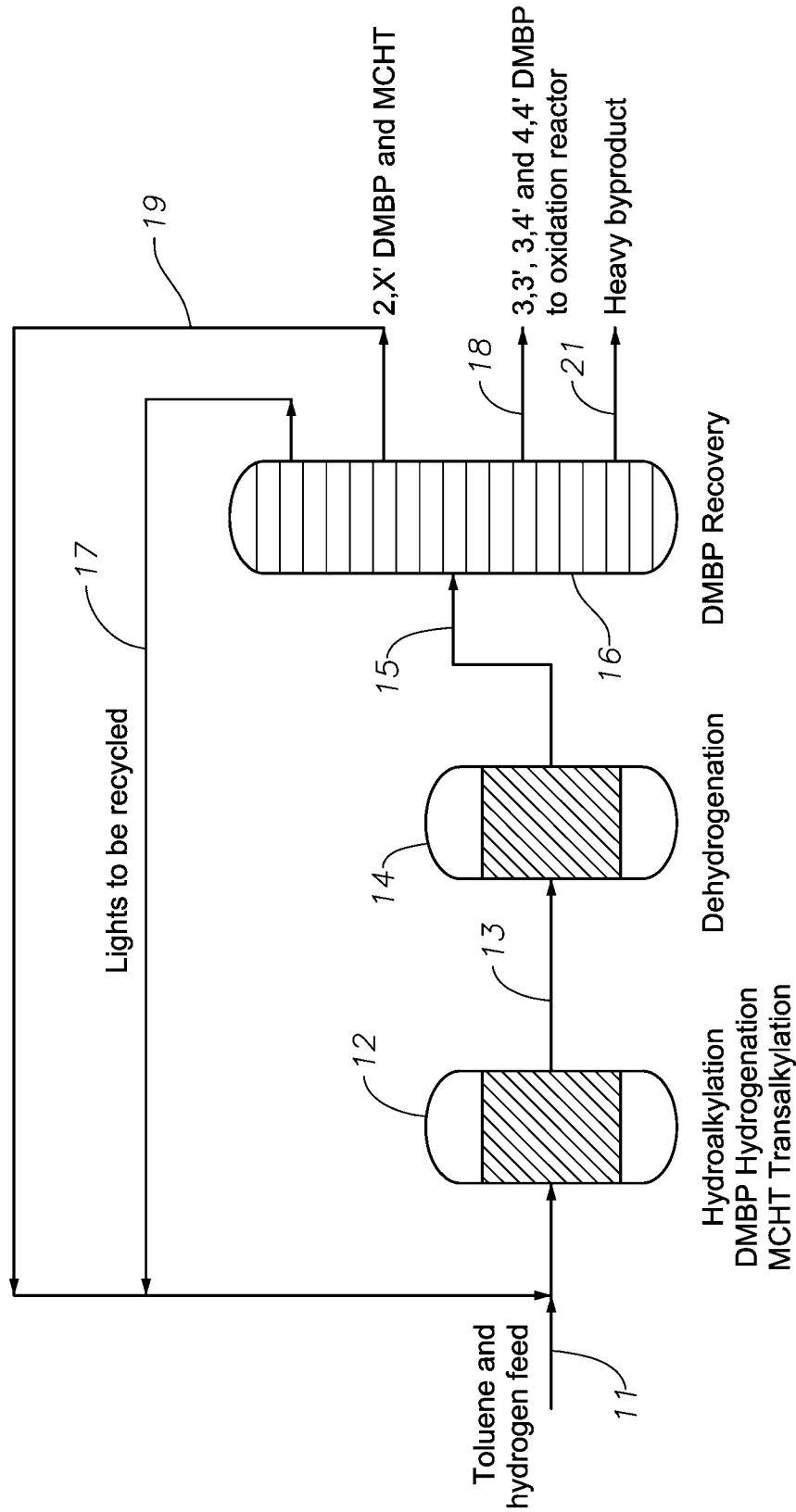
FIG. 2 is a flow diagram of a process for producing a mixture of dimethylbiphenyl isomers according to a further embodiment of the invention.

A second embodiment of a process for selectively converting toluene to 3,3'-, 3,4'- and 4,4'-DMBP is shown in FIG. 2, in which like numerals indicate like components to the process shown in FIG. 1. In the process shown in FIG. 2, rather than being supplied to a separate isomerization section, the second intermediate stream, rich in 2,X'-DMBP isomers and residual MCHT, is recycled by line 19 to the hydroalkylation unit 12. In this way, the hydrogenation of the 2,X'-DMBP isomers in the second intermediate stream and transalkylation of the resulting MCHT are conducted in the same reactor as that used to hydroalkylate the toluene feed. To assist this combination of reactions, a transalkylation catalyst can be included in the hydroalkylation unit 12 in addition to the hydroalkylation catalyst.

The invention will now be more particularly described with reference to the following non-limiting Examples and FIGS. 3 and 4 of the accompanying drawings.

This invention further relates to:

1. A process for producing dialkylbiphenyl compounds, the process comprising:
    (a1) providing a feed comprising substituted cyclohexylbenzene isomers having the formula (I):

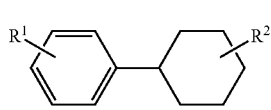

(I)

wherein each of $R^1$ and $R^2$ is an alkyl group and wherein the feed comprises m % by weight of isomers in which $R^1$ is in the 2-position, based on the total weight of substituted cyclohexylbenzene isomers in the feed;

(a2) reacting the feed under transalkylation conditions with a compound of formula (II):

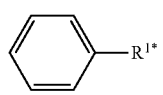

(II)

where $R^{1*}$ is an alkyl group, to produce a transalkylation product comprising substituted cyclohexylbenzene isomers having the formula (I) and including n % by weight of isomers in which $R^1$ is in the 2-position, based on the total weight of substituted cyclohexylbenzene isomers in the transalkylation product, wherein n<m; and (a3) dehydrogenating at least part of the transalkylation product under conditions effective to convert at least part of the substituted cyclohexylbenzene isomers in the transalkylation product to dialkylbiphenyl compounds.

2. The process of paragraph 1, wherein each of $R^{1*}$, $R^1$ and $R^2$ is a methyl group.

3. The process of paragraph 1 or 2, wherein the reacting (a2) is conducted at a temperature of 75 to 250° C.

4. The process of any of paragraphs 1 to 3, wherein the reacting (a2) is conducted in the presence of a solid acid catalyst.

5. The process of any of paragraphs 1 to 4, wherein the reacting (a2) is conducted in the presence of a solid acid catalyst comprising zeolite Y, beta or mordenite.

6. The process of any of paragraphs 1 to 5, wherein m is at least 15 wt % and n is less than 60 wt %.

7. A process for reducing the amount of 2,X' dialkylbiphenyl isomers (where X' is 2', 3' and/or 4') in a first mixture containing the same, the process comprising:

(b1) hydrogenating the first mixture under conditions effective to produce a hydrogenation product comprising substituted cyclohexylbenzene isomers having the formula (I):

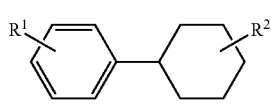

(I)

wherein each of $R^1$ and $R^2$ is an alkyl group and wherein the hydrogenation product comprises m % by weight of isomers in which $R^1$ is in the 2-position, based on the total weight of substituted cyclohexylbenzene isomers in the hydrogenation product;

(b2) reacting the hydrogenation product under transalkylation conditions with a compound of formula (II):

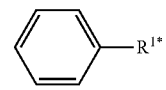

(II)

wherein $R^{1*}$ is an alkyl group, to produce a transalkylation product comprising substituted cyclohexylbenzene isomers having the formula (I) and including n % by weight of isomers in which $R^1$ is in the 2-position, based on the total weight of substituted cyclohexylbenzene isomers in the transalkylation product, wherein n<m; and (b3) dehydrogenating at least part of the substituted cyclohexylbenzene isomers in the transalkylation product to produce a product mixture containing less 2,3' and 2,4' dialkylbiphenyl isomers than the first mixture.

8. The process of paragraph 7, wherein each of $R^{1*}$, $R^1$ and $R^2$ is a methyl group.

9. The process of paragraph 7 or 8, wherein the reacting (b2) is conducted at a temperature of 75 to 250° C.

10. The process of any one of paragraphs 7 to 9, wherein the reacting (b2) is conducted in the presence of a solid acid catalyst.

11. The process of any one of paragraphs 7 to 10, wherein the reacting (b2) is conducted in the presence of a solid acid catalyst comprising zeolite Y, beta or mordenite.

12. The process of any one of paragraphs 7 to 11, wherein m is at least 15 wt % and n is less than 60 wt %.

13. A process for producing dimethylbiphenyl compounds, the process comprising:

(c1) contacting toluene with hydrogen under hydroalkylation conditions effective to produce a hydroalkylation product comprising (methylcyclohexyl)toluenes;

(c2) dehydrogenating at least part of the hydroalkylation product under conditions effective to produce a first dehydrogenation product comprising dimethylbiphenyl isomers and unreacted (methylcyclohexyl)toluenes;

(c3) separating the first dehydrogenation product into a first fraction comprising one or more 3,3', 3,4' and 4,4' dimethylbiphenyl isomers and a second fraction comprising one or more 2,X'-dimethylbiphenyl isomers (where X' is 2, 3, or 4) and at least part of the unreacted (methylcyclohexyl) toluenes;

(c4) hydrogenating at least part of the dimethylbiphenyl isomers in the second fraction to the corresponding (methylcyclohexyl)toluene isomers and produce a hydrogenation effluent;

(c5) reacting at least part of the hydrogenation effluent from (c4) with toluene under transalkylation conditions affective to produce a transalkylation product containing less material represented by Formula (X) than the hydrogenation effluent, where Formula (X) is

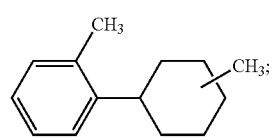

and (c6) dehydrogenating at least part of the transalkylation product to produce a second dehydrogenation product comprising less 2,X'-dimethylbiphenyl isomers than the first dehydrogenation product.

14. The process of paragraph 13, wherein the contacting (c1) and the reacting (c5) are conducted in sequential reaction zones.

15. The process of paragraph 13, wherein the contacting (c1) and the reacting (c5) are conducted in the same reaction zone.

16. The process of any one of paragraphs 13 to 15, wherein the hydrogenating (c4) and the reacting (c5) are conducted in sequential reaction zones.

17. The process of any one of paragraphs 13 to 15, wherein the hydrogenating (c4) and the reacting (c5) are conducted in the same reaction zone.

18. The process of paragraph 13, wherein the contacting (c1), the hydrogenating (c4) and the reacting (c5) are conducted in the same reaction zone.

19. The process of paragraph 18, wherein the reaction zone contains a catalyst composition comprising a molecular sieve of the MCM-22 family, a FAU-type molecular sieve and a hydrogenation/dehydrogenation component.

20. The process of any preceding paragraph, wherein m is at least 5 wt % and n is less than 75 wt %.

21. The process of any of paragraphs 1 to 20, wherein the catalyst used for hydrogenation in step (b1) comprises a transition metal.

22. The process of paragraph 21, wherein the metal is a Group 3, 4, 5, 6, 7, 8, 9, 10, 11, or 12 metal.

23. The process of paragraph 22, wherein the metal is Pt or Pd.

Example 1

The experiments described in Examples 1 and 2 utilized a reactor unit with 8 parallel reactors heated by furnace. For different tests anywhere from 1-8 reactors could be utilized. The reactors used in these experiments consisted of quartz tubes of 9 mm in diameter. Annular $N_2$ flow on the outside of the quartz reactor allowed for pressure equilibration between the inside and outside of each reactor channel. Catalyst extrudates were crushed to 20/40 mesh loaded in quantities ranging from 0.25-2 g (to vary corresponding weight based space velocity) after being diluted up to 4 g in crushed quartz. A quartz wool plug was used at the top and bottom of the catalyst bed to keep catalyst in place. Two sets of 4 parallel reactors were placed in heated furnaces to control isothermal reaction temperature. Each reactor contained an internal thermocouple in the catalyst bed in a 1/8" thermowell. The reactors were topped off with the same quartz chips.

The catalysts in all reactors were pre-conditioned in situ as described in the subsequent Examples. An ISCO syringe pump was used to introduce the feed to the reactor. The feed was pumped through a vaporizer before being mixed in-line with $H_2$ and/or $N_2$ at a molar ratio of between 0 and 2 (gas to hydrocarbon liquid). The products exiting the reactor were condensed and collected in intervals (1-2 samples per day per reactor) and analyzed offline by GC or GCMS.

GC analysis was conducted on an Agilent 7890 GC equipped with FID detector and an Automatic liquid sampler (ALS). Typical injection size was about 0.2 μl. The columns used were from Supelco of the Dex type. A Gamma DEX column was joined together with a Beta Dex column to give a total length of 120 m (60 m for each type). The ID of the columns was 0.25 mm. The GC was operated in constant flow mode with an I\initial pressure of about 78 psi and column flow of about 3.0 ml/min using helium as carrier gas. The following oven procedure was employed:

Initial temperature of 140° C., hold for 30 minutes
Ramp 1 at 2° C./min to 180° C., hold for 20 minutes
Ramp 2 at 3° C./min to 220° C., hold for 7 minutes
Total analysis time of 90.33 minutes.

A similar method was used for the GC-MS measurements. The instrument was an Agilent 7890 GC equipped with a 5975C MSD detector and FID. The main difference is that this setup had a purged 2-way splitter that enabled a sample to be simultaneously analyzed on two detectors using a single injection. The injection size was about 0.5 μl. Additionally, an auxiliary helium pressure of 6 psi was used for the purged splitter. The final oven time was extended by 20 minutes for a total analysis time of 110 minutes.

In Example 1, one reactor of the reactor unit described above was utilized to study the transalkylation of cyclohexylbenzene (CHB) with toluene. 1 gram of a commercial USY catalyst was loaded into the reactor channel and the catalyst was dried in $N_2$ overnight at 260° C. A liquid feed consisting of 33% cyclohexylbenzene and 67% toluene by weight was fed to the reactor at 1 WHSV with a co-feed of nitrogen at a 0.7:1 nitrogen to hydrocarbon molar ratio.

Figure 3:
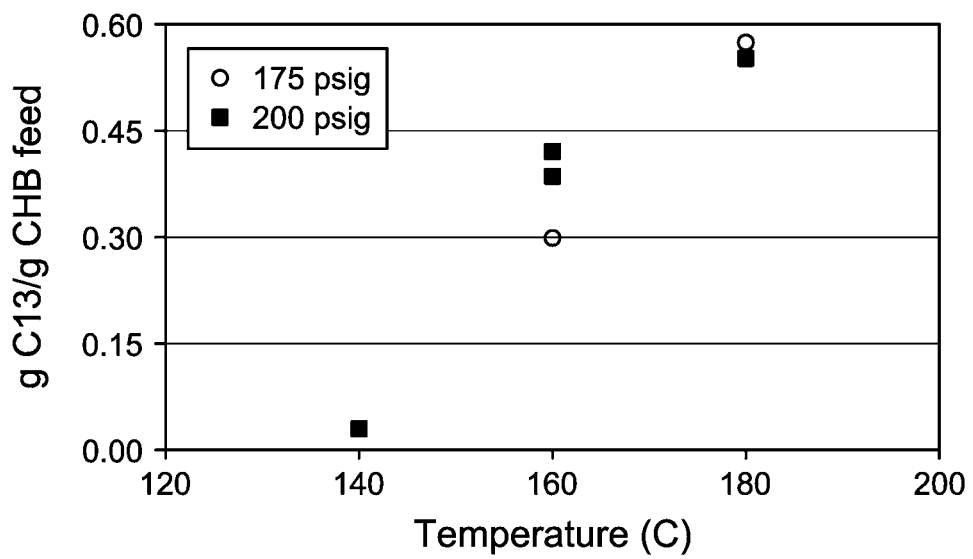
FIG. 3 is a graph of $C_{13}$ yield as a function of temperature at different pressures in the translkylation of cyclohexylbenzene with toluene according to Example 1.
Figure 4:
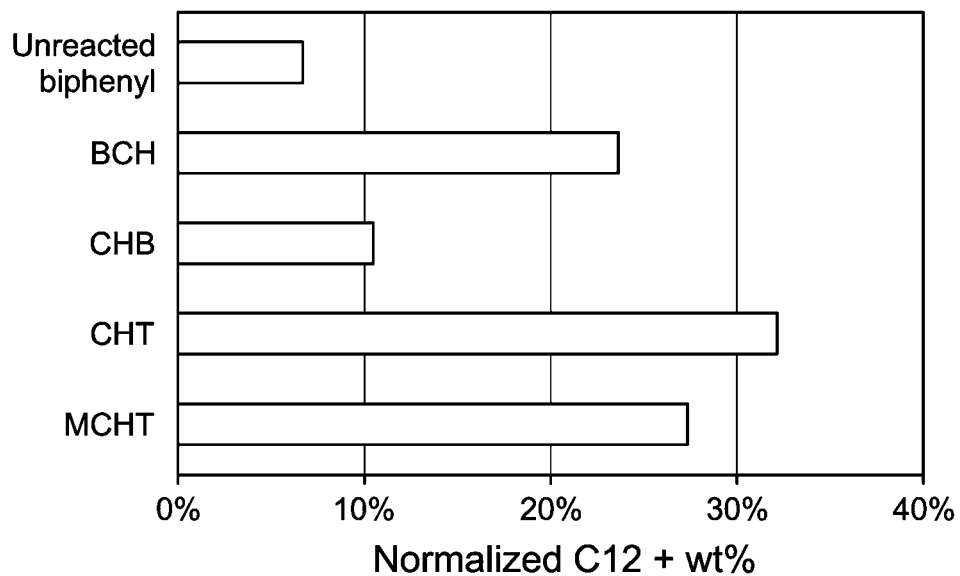
FIG. 4 is bar graph showing the normalized weight percent of major reactor effluent liquid species of carbon number 12 or higher for the sequential hydrogenation and transalkylation process of Example 2.

The results are shown in FIG. 3 and Table 1 below.

TABLE 1

| Temperature (° C.) | 180 | 160 | 160 | 180 |
|---|---|---|---|---|
| Pressure (psig) | 200 | 200 | 175 | 175 |
| Cyclohexylbenzene (CHB) conversion | 87% | 44% | 28% | 86% |
| Moles $C_{13}H_{18}$/Moles CHB consumed | 59% | 88% | 100% | 62% |

In Example 1, CHB is used as a surrogate for MCHT to test the viability of transalkylation to change the isomer distribution of MCHT. FIG. 3 shows the yield of $C_{13}$ products (g produced per g CHB fed) as a function of temperature and pressure. The rates at 140° C. are low, but significant. The yield increases with temperature as is seen in Table 1 and FIG. 3. These results prove the concept that MCHT transalkylation with toluene can be used to effectively change the methyl group position on the aromatic ring of the molecules. Undesired products include CHB decomposition to benzene and alkanes as well as xylene formation and the formation of heavier species. In these experiments, the xylene yield was less than 0.001 g/g in all cases. This means that transalkylation of toluene at the benzylic carbon of CHB is much more favorable than methyl disproportionation.

Example 2

The procedure and apparatus of Example 1 were employed but with one reactor channel being utilized to study the sequential hydrogenation and transalkylation of biphenyl in a stacked bed configuration. 1 gram each of a commercial platinum/palladium hydrogenation catalyst and a commercial USY catalyst were loaded in a stacked bed configuration with the hydrogenation catalyst upstream of the zeolite catalyst. The catalysts were dried in $N_2$ overnight at 260° C. and then a reduction procedure followed where 5 sccm $H_2$ was flowed over the bed at 50 psig and the temperature was ramped at 5° C./min to 290° C. This temperature was held for 3 hours and then the reactor was cooled to the starting reaction temperature of 200° C. A liquid feed consisting of 10% biphenyl and 90% toluene by weight was fed to the reactor at 1 WHSV (total) with a co-feed of hydrogen at a 2:1 hydrogen to hydrocarbon molar ratio.

In this example, at 200° C. and 200 psig (1480 kPa-absolute), greater than 90% of the biphenyl in the feed was converted. The major $C_{12}$ or greater products were cyclohexylbenzene (CHB) and bicyclohexane (BCH) from hydrogenation of the biphenyl, cyclohexyltoluene (CHT, $C_{13}H_{18}$) from the desired sequence of hydrogenation and transalkylation, and methylcyclohexyltoluene (MCHT) which was likely a result of toluene hydroalkylation over the multiple catalyst functions. The normalized distribution of these products in the reactor effluent liquid is shown in FIG. 5.

Example 3

In this Example, a study was conducted on the sequential hydrogenation and toluene transalkylation of dimethylbiphenyl in a mixed bed configuration with simultaneous toluene transalkylation. The reaction test was carried out in a fixed bed down-flow reactor having a diameter of 0.5 inch (1.3 cm). The catalysts used in the study were a mixed bed of commercial USY/$Al_2O_3$ and Pd/MCM-49 hydroalkylation catalyst (in varying ratio). The catalyst charge was 4 g. The catalyst was activated by heating up the catalyst bed to 260° C. under nitrogen and drying overnight. The catalyst was then reduced in hydrogen at 290° C. (ramp rate of 5° C./min) for 3 hours. Hydrogen flow rate was 50 sccm. Reactor pressure was maintained constant, at 50 psig (346 kPa-absolute), throughout catalyst activation.

The liquid feed used in this test was a mixture of 90% anhydrous toluene and 10% 2,3' DMBP. Hydrogen to hydrocarbon ratio of 2:1 (molar) was used. The total WHSV used in this experiment was 1, the reaction pressure was 175 psig (1308 kPa-absolute) and the temperature was 165° C. or 185° C. The results are shown in Table 2 below:

TABLE 2

| Ratio USY:Pd/MCM-49 | 1 | 1 | 3 |
|---|---|---|---|
| Time on stream (days) | 3 | 6 | 3 |
| Temperature (° C.) | 165 | 185 | 165 |
| Pressure (psig) | 175 | 175 | 175 |
| 2,3' DMBP conversion | 38% | 57% | 53% |
| Toluene conversion | 47% | 24% | 28% |
| g 2,3' DMBP/g product | 6% | 4% | 5% |
| g 2,X' MCHT/g product | 5% | 4% | 5% |
| g bimethylcyclohexane (BCMH)/g product | 2% | 1% | 1% |

As is seen in Table 2, this configuration allows for the consumption of 2,3' DMBP with simultaneous hydroalkylation. It also shows the viability of consuming 2,X' DMBP and 2,X' MCHT at the same rate as 2,X' MCHT is being produced by the hydroalkylation reaction. It should be noted that direct isomerization of the 2,3' DMBP is also a possible reaction pathway for consumption in addition to the sequential hydrogenation and transalkylation described here.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

All documents described herein are incorporated by reference herein, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law. Likewise whenever a composition, an element or a group of elements is preceded with the transitional phrase "comprising", it is understood that we also contemplate the same composition or group of elements with transitional phrases "consisting essentially of," "consisting of", "selected from the group of consisting of," or "is" preceding the recitation of the composition, element, or elements and vice versa.

What is claimed is:

1. A process for producing dialkylbiphenyl compounds, the process comprising:
    (a1) providing a feed comprising substituted cyclohexylbenzene isomers having the formula (I):

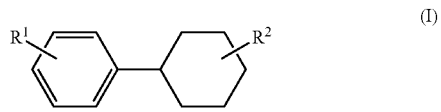

wherein each of $R^1$ and $R^2$ is an alkyl group and wherein the feed comprises m % by weight of isomers in which $R^1$ is in the 2-position, based on the total weight of substituted cyclohexylbenzene isomers in the feed;
    (a2) reacting the feed under transalkylation conditions with a compound of formula (II):

where $R^{1*}$ is an alkyl group,
    to produce a transalkylation product comprising substituted cyclohexylbenzene isomers having the formula (I) and including n % by weight of isomers in which $R^1$ is in the 2-position, based on the total weight of substituted cyclohexylbenzene isomers in the transalkylation product, wherein n<m; and
    (a3) dehydrogenating at least part of the transalkylation product under conditions effective to convert at least part of the substituted cyclohexylbenzene isomers in the transalkylation product to dialkylbiphenyl compounds.

2. The process of claim 1, wherein each of $R^{1*}$, $R^1$ and $R^2$ is a methyl group.

3. The process of claim 1, wherein the reacting (a2) is conducted at a temperature of 75 to 250° C.

4. The process of claim 1, wherein the reacting (a2) is conducted in the presence of a solid acid catalyst.

5. The process of claim 1, wherein the reacting (a2) is conducted in the presence of a solid acid catalyst comprising zeolite Y, beta or mordenite.

6. The process of claim 1, wherein m is at least 15 wt % and n is less than 60 wt %.

7. A process for reducing the amount of 2,X' dialkylbiphenyl isomers (where X' is 2', 3', and/or 4') in a first mixture containing the same, the process comprising:

(b1) hydrogenating the first mixture under conditions effective to produce a hydrogenation product comprising substituted cyclohexylbenzene isomers having the formula (I):

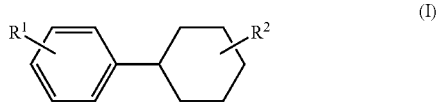

wherein each of $R^1$ and $R^2$ is an alkyl group and wherein the hydrogenation product comprises m % by weight of isomers in which $R^1$ is in the 2-position, based on the total weight of substituted cyclohexylbenzene isomers in the hydrogenation product;

(b2) reacting the hydrogenation product under transalkylation conditions with a compound of formula (II):

where $R^{1*}$ is an alkyl group,
to produce a transalkylation product comprising substituted cyclohexylbenzene isomers having the formula (I) and including n % by weight of isomers in which $R^1$ is in the 2-position, based on the total weight of substituted cyclohexylbenzene isomers in the transalkylation product, wherein n<m; and (b3) dehydrogenating at least part of the substituted cyclohexylbenzene isomers in the transalkylation product to produce a product mixture containing less 2,3' and 2,4' dialkylbiphenyl isomers than the first mixture.

8. The process of claim 7, wherein each of $R^1$ and $R^2$ is a methyl group.

9. The process of claim 7, wherein the reacting (b2) is conducted at a temperature of 75 to 250° C.

10. The process of claim 7, wherein the reacting (b2) is conducted in the presence of a solid acid catalyst.

11. The process of claim 7, wherein the reacting (b2) is conducted in the presence of a solid acid catalyst comprising zeolite Y, beta or mordenite.

12. The process of claim 7, wherein m is at least 15 wt % and n is less than 60 wt %.

13. A process for producing dimethylbiphenyl compounds, the process comprising:
(c1) contacting toluene with hydrogen under hydroalkylation conditions effective to produce a hydroalkylation product comprising (methylcyclohexyl)toluenes;
(c2) dehydrogenating at least part of the hydroalkylation product under conditions effective to produce a first dehydrogenation product comprising dimethylbiphenyl isomers and unreacted (methylcyclohexyl)toluenes;
(c3) separating the first dehydrogenation product into a first fraction comprising one or more 3,3', 3,4' and 4,4' dimethylbiphenyl isomers and a second fraction comprising one or more 2,X'-dimethylbiphenyl isomers (where X' is 2, 3 or 4) and at least part of the unreacted (methylcyclohexyl)toluenes;
(c4) hydrogenating at least part of the dimethylbiphenyl isomers in the second fraction to the corresponding (methylcyclohexyl)toluene isomers and produce a hydrogenation effluent;
(c5) reacting at least part of the hydrogenation effluent from (c4) with toluene under transalkylation conditions effective to produce a transalkylation product containing less material represented by Formula (X) than the hydrogenation effluent, where Formula (X) is

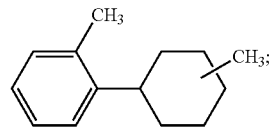

and
(c6) dehydrogenating at least part of the transalkylation product to produce a second dehydrogenation product comprising less 2,X'-dimethylbiphenyl isomers than the first dehydrogenation product.

14. The process of claim 13, wherein the contacting (c1) and the reacting (c5) are conducted in sequential reaction zones.

15. The process of claim 13, wherein the contacting (c1) and the reacting (c5) are conducted in the same reaction zone.

16. The process of claim 13, wherein the hydrogenating (c4) and the reacting (c5) are conducted in sequential reaction zones.

17. The process of claim 13, wherein the hydrogenating (c4) and the reacting (c5) are conducted in the same reaction zone.

18. The process of claim 13, wherein the contacting (c1), the hydrogenating (c4) and the reacting (c5) are conducted in the same reaction zone.

19. The process of claim 18, wherein the reaction zone contains a catalyst composition comprising a molecular sieve of the MCM-22 family, a FAU-type molecular sieve and a hydrogenation/dehydrogenation component.

20. The process of claim 13, wherein the hydrogenating (c4) catalyst function and the hydrogenation function of the hydroalkylation (c1) catalyst are performed by the same metal in the same reaction zone.

21. The process of claim 13, wherein the transalkylation (c5) catalyst function and the alkylation function of the hydroalkylation (c1) catalyst are performed by the same solid acid catalyst in the same reaction zone.

22. The process of claim 1, wherein m is at least 5 wt % and n is less than 75 wt %.

23. The process of claim 7, wherein m is at least 5 wt % and n is less than 75 wt %.

24. The process of claim 7, wherein the catalyst used for hydrogenation in step (b1) comprises a transition metal.

25. The process of claim 24, wherein the metal is a Group 3, 4, 5, 6, 7, 8, 9, 10, 11 or 12 metal.

26. The process of claim 24, wherein the metal is Pt or Pd.

* * * * *